(12) United States Patent
Nourani et al.

(10) Patent No.: US 11,090,438 B2
(45) Date of Patent: Aug. 17, 2021

(54) SLANTED SYRINGE HANDLE

(71) Applicant: Bobby Nourani, Madison, WI (US)

(72) Inventors: Bobby Nourani, Madison, WI (US);
Jared Muench, Manitowoc, WI (US);
Katherine Konsor, Deer Park, IL (US);
Matthew McMillan, Orono, MN (US);
Caroline Brumley, Ripon, WI (US);
Jennifer Leestma, Wayzata, MN (US);
Christopher Thomas, Lone Park, WI (US)

(73) Assignee: Bobby Nourani, Madison, WI (US)

( * ) Notice: Subject to any disclaimer, the term of this patent is extended or adjusted under 35 U.S.C. 154(b) by 195 days.

(21) Appl. No.: 16/162,637

(22) Filed: Oct. 17, 2018

(65) Prior Publication Data

US 2019/0184106 A1 Jun. 20, 2019

Related U.S. Application Data

(60) Provisional application No. 62/573,648, filed on Oct. 17, 2017.

(51) Int. Cl.
*A61M 5/31* (2006.01)
(52) U.S. Cl.
CPC ........ *A61M 5/3137* (2013.01); *A61M 5/3134* (2013.01); *A61M 2005/3139* (2013.01); *A61M 2205/586* (2013.01)
(58) Field of Classification Search
CPC .......... A61M 2205/586; A61M 5/3137; A61M 2005/3139; A61M 5/3135
See application file for complete search history.

(56) References Cited

U.S. PATENT DOCUMENTS

| | | | |
|---|---|---|---|
| 2,585,815 A * | 2/1952 | McLintock | A61M 5/20 604/209 |
| 4,767,413 A | 8/1988 | Haber et al. | |
| 5,927,562 A | 7/1999 | Hammen et al. | |
| 10,398,841 B2 | 9/2019 | Evans et al. | |
| 10,537,683 B2 | 1/2020 | Ruddocks et al. | |
| 10,576,209 B2 | 3/2020 | Lum et al. | |
| 10,596,321 B2 | 3/2020 | Mandaroux et al. | |
| 2007/0249994 A1 | 10/2007 | Uhlin et al. | |
| 2008/0051729 A1 | 2/2008 | Cheng | |
| 2012/0095438 A1 | 4/2012 | Lanin et al. | |

(Continued)

FOREIGN PATENT DOCUMENTS

| | | |
|---|---|---|
| CN | 2225258 Y | 4/1996 |
| CN | 106983935 A | 7/2017 |

(Continued)

*Primary Examiner* — Emily L Schmidt
(74) *Attorney, Agent, or Firm* — Brentwood IP Law, P.C.; Shahrooz Isaac Zaghi

(57) ABSTRACT

Example syringe handles including a hub portion and a grip portion. The hub portion includes an outer surface, an inner surface configured to receive a portion of a syringe body, and a top and bottom surface each being adjacent to both the outer surface and the inner surface. The grip portion includes a first and a second arm, each connected to and extending from the outer surface of the hub portion. The first arm includes a distal end biased toward the top surface of the hub portion and the second arm includes a distal end biased toward the top surface of the hub portion.

16 Claims, 6 Drawing Sheets

(56) References Cited

U.S. PATENT DOCUMENTS

| | | | | |
|---|---|---|---|---|
| 2013/0303993 | A1* | 11/2013 | Evans | A61M 5/31 604/227 |
| 2016/0101238 | A1* | 4/2016 | Evans | A61M 5/3137 604/227 |
| 2016/0144120 | A1 | 5/2016 | Ishikawa et al. | |
| 2018/0071462 | A1 | 3/2018 | Morgan et al. | |
| 2018/0256828 | A1 | 9/2018 | Sirianni | |
| 2019/0030253 | A1 | 1/2019 | Barbour | |
| 2019/0183674 | A1 | 6/2019 | Tsai et al. | |
| 2019/0351146 | A1 | 11/2019 | Franklin et al. | |
| 2020/0078528 | A1 | 3/2020 | Heim et al. | |

FOREIGN PATENT DOCUMENTS

| | | |
|---|---|---|
| DE | 202019102126 U1 | 7/2019 |
| FR | 2830199 A1 | 4/2003 |
| JP | 2004527333 A | 9/2004 |
| KR | 0138353 Y1 | 4/1999 |
| WO | 2005060367 A3 | 7/2006 |
| WO | 2008016381 A1 | 2/2008 |
| WO | 2017039786 A1 | 3/2017 |
| WO | 2017184801 A1 | 10/2017 |

* cited by examiner

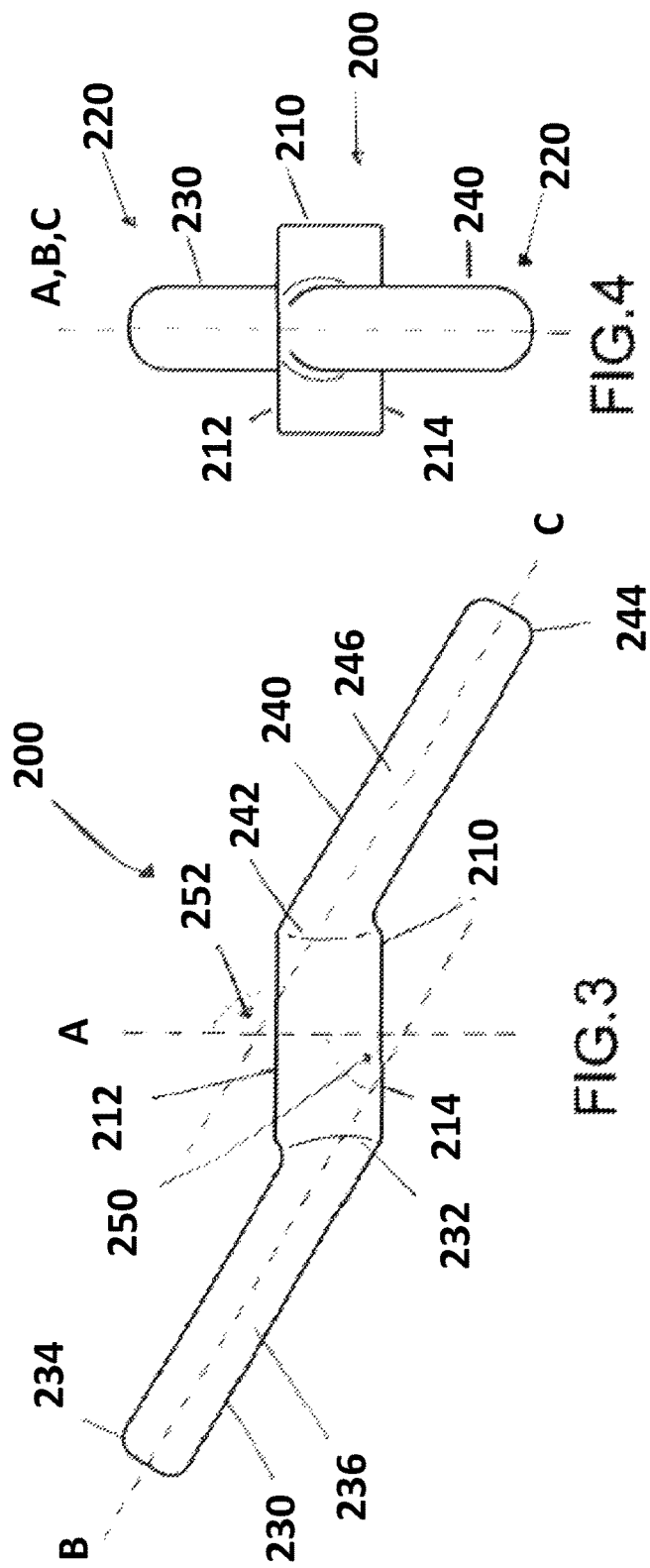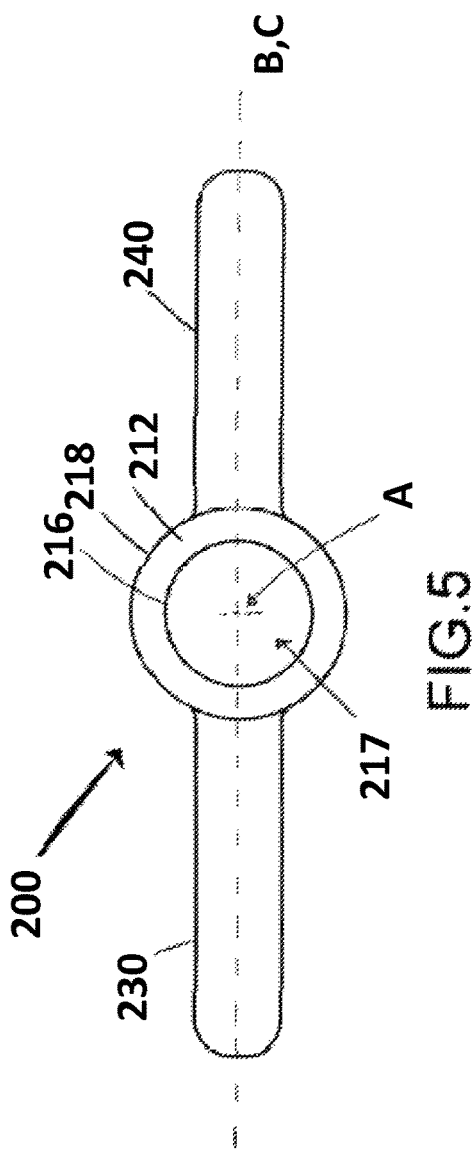

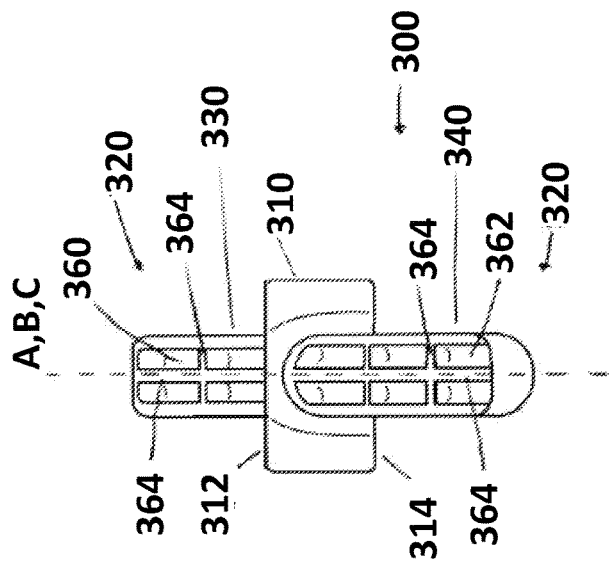
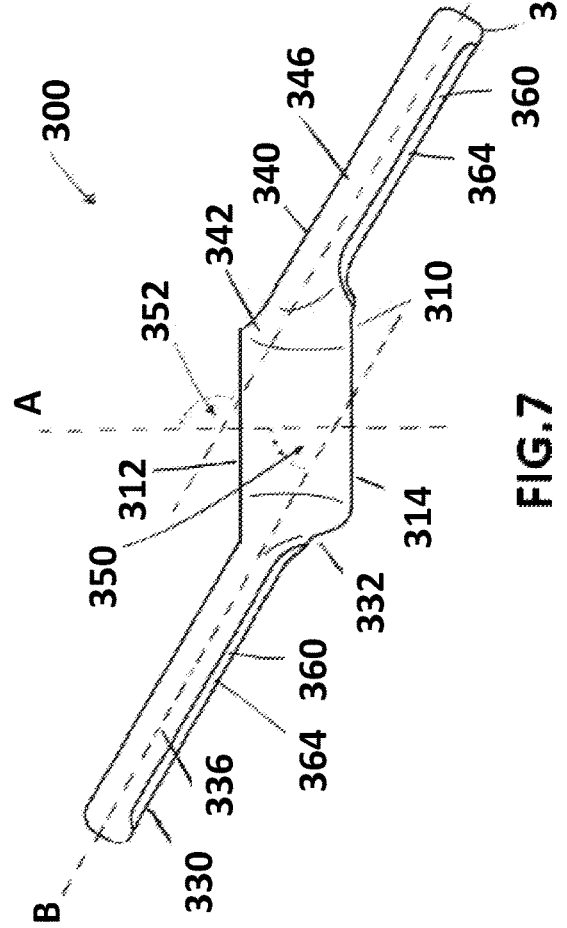
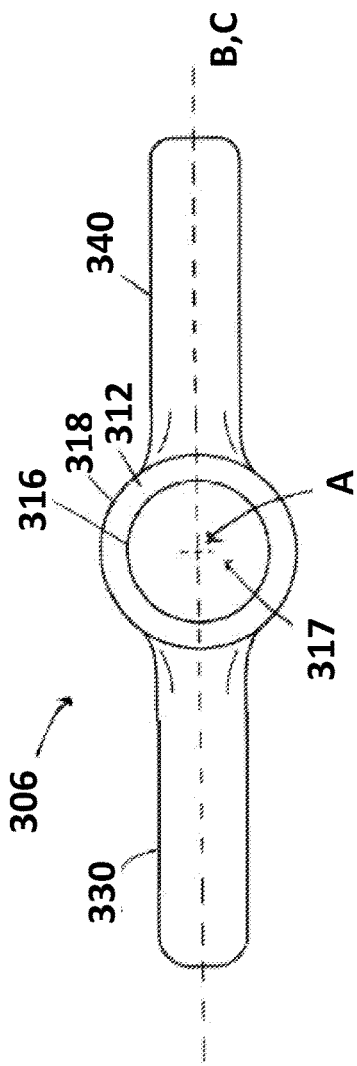
FIG.8
FIG.7
FIG.9

SLANTED SYRINGE HANDLE

CROSS-REFERENCE TO RELATED APPLICATION

The present application is related to U.S. Provisional Patent Application No. 62/573,648, filed Oct. 17, 2017, the entire contents of which are incorporated herein by reference.

FIELD OF THE DISCLOSURE

The present disclosure is directed to syringes, which can be used to deliver medications as well as to inject and to extract fluids. More specifically, the present disclosure relates to handles for syringes.

INTRODUCTION

Since their beginnings in 1961 by the medical supply company Becton Dickinson, syringes have transformed the way medical professionals are able to deliver drugs, inject medications, and extract fluids. A typical syringe includes a syringe body and a plunger movably positioned within the syringe body. The syringe body generally includes a barrel portion where the fluid to be injected is contained, an open end configured to receive the plunger, a necked end configured to receive a needle, and a flange

SUMMARY

This disclosure relates to syringe handles and features of syringe handles that distribute the force used to operate a syringe and to reduce fatigue.

In general, a syringe handle includes a hub portion and a grip portion. The hub portion defines an inner surface configured to receive the body of a syringe, an outside surface, a top surface and a bottom surface. The grip portion includes first and second arms which are connected to and extend from the outside surface of the hub portion. The first arm is biased toward the top surface of the hub portion and the second arm is biased toward the bottom surface of the hub portion.

The user of the syringe handle inserts the body of a syringe into the channel defined by the inner surface of the hub portion of the syringe handle. The handle is inserted such that either the top surface or the bottom surface of the hub abuts the flange of the syringe. In typical operation, the user depresses the plunger of the syringe by placing their thumb on the plunger and a number of fingers on the syringe handle.

The orientation of the arms on the syringe handle positions a user's hand in an ergonomically advantageous position during use of the syringe. In addition, the arms provide a greater surface area for the user to place their fingers while depressing the plunger of a syringe. By facilitating an ergonomically advantageous position and increasing the surface area, the user is better able to control the syringe during injections. In addition, the increased surface area allows the user to apply more force to the plunger and reduces the relative pressure on the fingers of the user which would otherwise be in contact with the flange of the syringe. This results in the user experiencing less fatigue when performing multiple injections, as is done, for example, in prolotherapy.

The details of one or more embodiments are set forth in the accompanying drawings and the description below. Other features, objects, and advantages of these embodiments will be apparent from the description, drawings, and claims. Moreover, it is to be understood that both the foregoing summary of the disclosure and the following detailed description are exemplary and intended to provide further explanation without limiting the scope of the disclosure.

BRIEF DESCRIPTION OF THE DRAWINGS

The following figures, which form a part of this application, are illustrative of described technology and are not meant to limit the scope of the claims in any manner.

FIG. 3 is a front view of the syringe handle shown in FIG. 2.
FIG. 4 is a side view of the syringe handle shown in FIG. 2.
FIG. 5 is a bottom view of the syringe handle shown in FIG. 2.
FIG. 7 is a front view of the syringe handle shown in FIG. 6.
FIG. 8 is a side view of the syringe handle shown in FIG. 6.
FIG. 9 is a bottom view of the syringe handle shown in FIG. 6.

DETAILED DESCRIPTION

Figure 1:
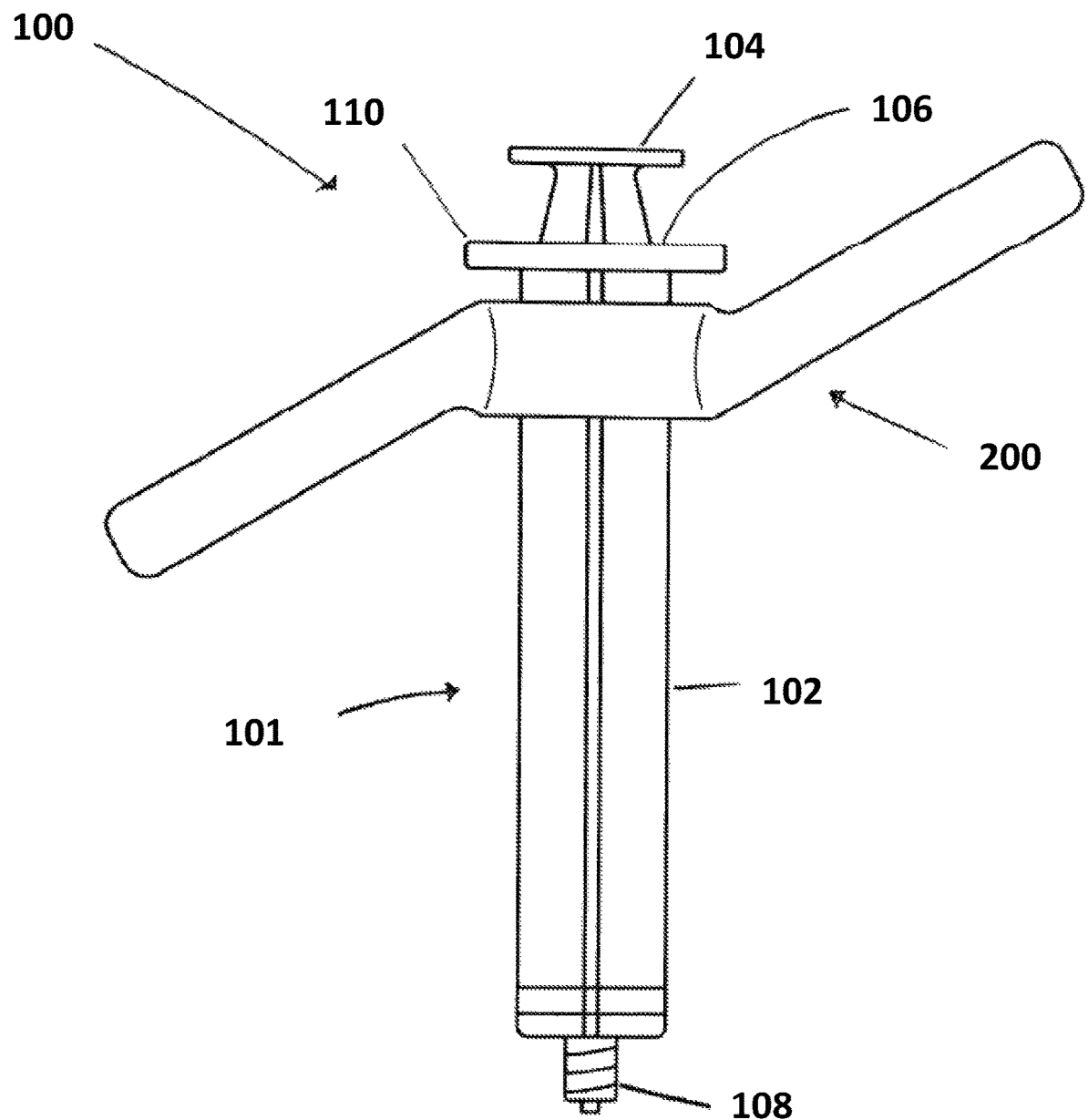
FIG. 1 is a front view of a syringe with a syringe handle.

Various embodiments of the present disclosure will be described in detail with reference to the drawings, wherein like reference numerals represent like parts and assemblies throughout the several views. The features described herein are examples of implementations of certain inventive aspects which underlie the disclosure.

As briefly described above, embodiments of the present disclosure are directed to syringe handles designed to provide an ergonomic grip. Syringe handles are described below as used with example syringes. In some instances, syringe handles disclosed and contemplated herein can be retrofit onto previously-manufactured syringes. In some instances, syringe handles disclosed and contemplated herein can be integral to a syringe body.

The syringe handle and its various described embodiments may be constructed from a variety of materials. In some instance it may be advantageous for the syringe handle to be made from metal or another sterilizable material to permit the syringe handle to be reused. In other instances, it may be advantageous for the syringe handle to be made of plastics, specifically medical grade plastics, resin, rubber, or fiberglass. The syringe handles described above may be made from a single material or any combination thereof.

Syringe use spans a variety of medical, biotech, and related fields, including prolotherapy, vaccination administration, blood transfusions, and laboratory bench science technicians, as well as both dental and veterinary applications. Typical operations of the syringe can cause discomfort over prolonged and repetitive use, indicating that the benefits from a more ergonomically advantageous syringe would be beneficial to a large variety of professionals.

Typical use of a syringe involves the user placing their thumb on the plunger of the syringe and placing two fingers on the flange of the syringe. The user then depresses the plunger of the syringe by applying force to both the plunger and the flange of the syringe. This results in the plunger being pushed into the barrel of the syringe which reduces the interior volume and forces the contained fluid through the necked end. The amount of force required to depress the syringe varies depending on the surface area of the plunger, volume of the syringe and the diameter of the needle attached to the necked end.

Physicians who utilize syringes on a frequent basis, particularly those performing injections, find that they experience discomfort, sometimes significantly, specifically in the hand and thumb. The pain experienced by these physicians is generally results from a high volume of fluid being ejected and increased resistance from sub-millimeter-wide needles. By reducing and potentially eliminating the pain experienced while using a syringe, physicians can reduce the number of workdays lost due to injury, and aging doctors, surgeons, laboratory technicians, dentists, and veterinarians can remain active longer into their careers.

FIG. 1 illustrates an example syringe 100. Syringe 100 generally includes a body portion 101 and a plunger 104. Body portion 101 includes a barrel portion 102 that receives a plunger 104 at open end 106 and a necked end 108, which can be configured to receive a needle. Open end 106 is surrounded by a flange 110 to allow for the user to grip the syringe 100 while depressing the plunger 104. Example syringe handle 200 is described in greater detail below with reference to FIGS. 2-5.

Figure 2:
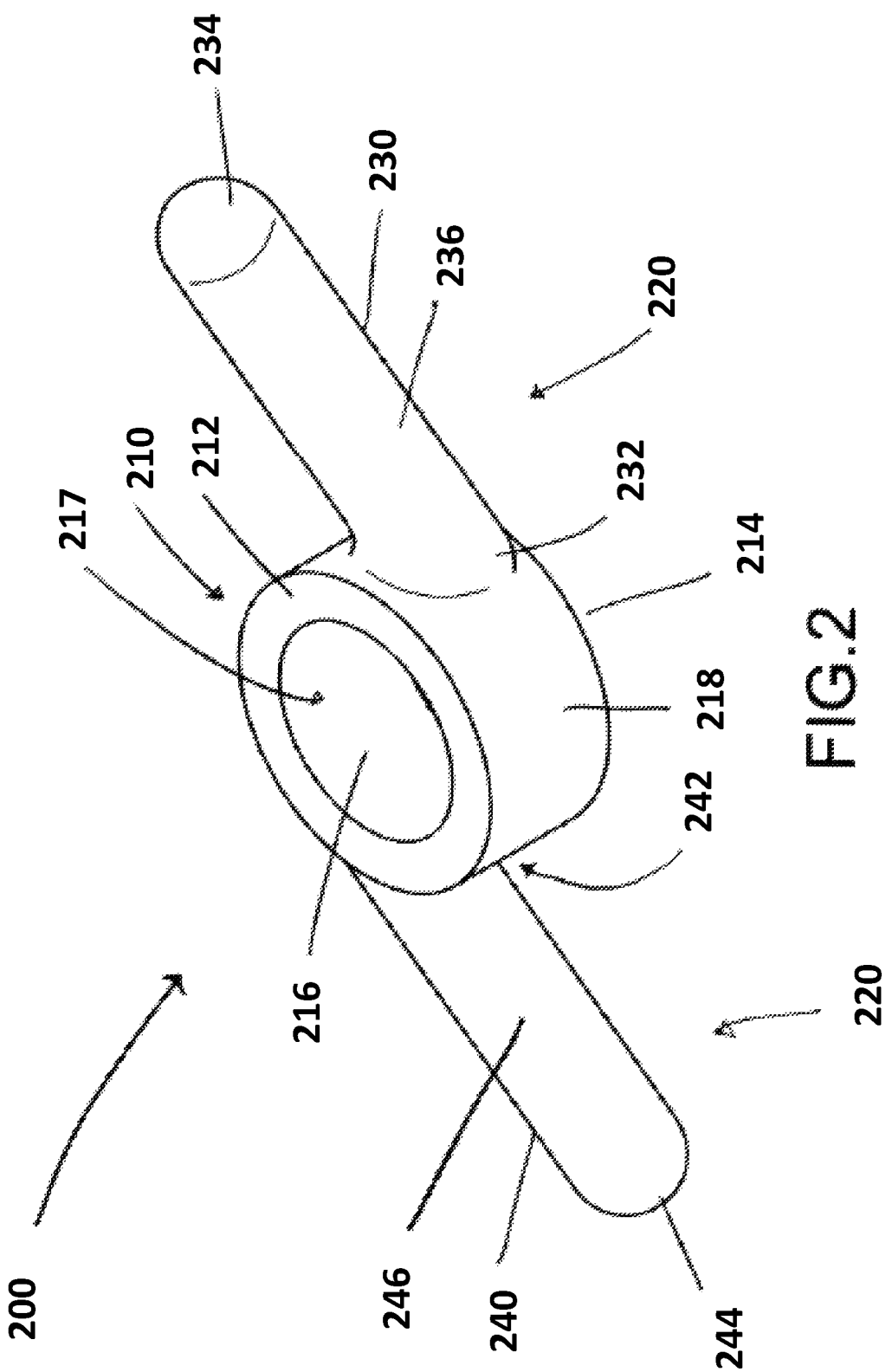
FIG. 2 is a front perspective view of a syringe handle.
Figure 6:
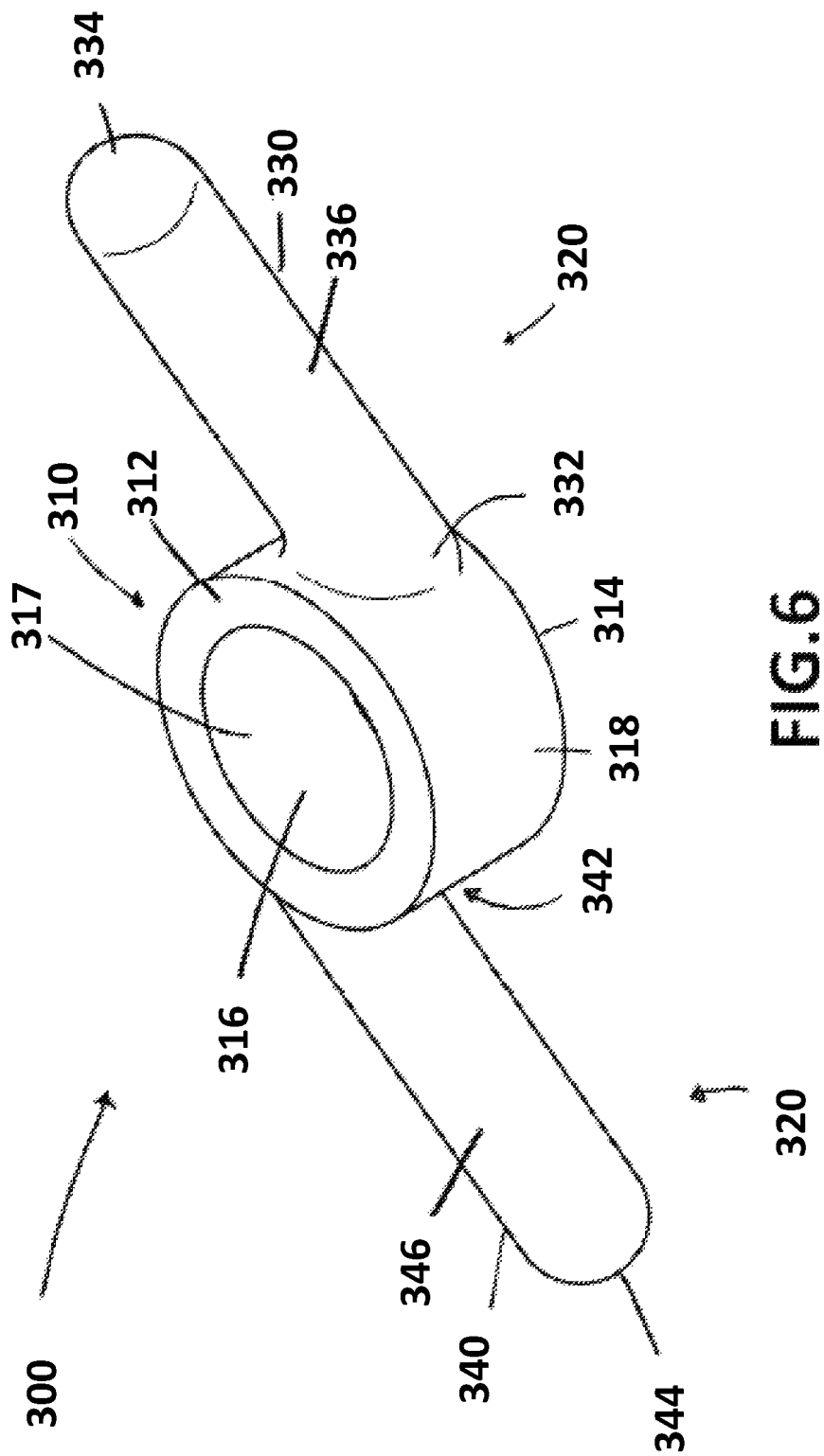
FIG. 6 is a front perspective view of another example embodiment of a syringe handle.

FIG. 2 illustrates a top perspective view of an example syringe handle 200. FIG. 3 illustrates a front view of syringe handle 200. FIG. 4 illustrates a side view of syringe handle 200. FIG. 5 illustrates a top view of syringe handle 200.

Syringe handle 200 includes a hub portion 210 and a grip portion 220. The hub portion 210 includes a top surface 212, a bottom surface 214, an inner surface 216 and an outer surface 218. Both inner surface 216 and outer surface 218 are disposed between top surface 212 and bottom surface 214.

Inner surface 216 forms a channel 217 in the hub portion 210 configured to receive a syringe barrel 102. Inner surface 216 is generally curved and configured to receive syringe barrel 102 and includes an axis A. Axis A is positioned along the length of the channel 217 defined by inner surface 216 and passes through the center of gravity of the channel 217. In some embodiments, inner surface 216 is cylindrical and axis A is a central axis passing through the channel 217 defined by inner surface 216. In other embodiments, inner surface 216 may be configured to accommodate different syringe barrel 102 shapes. The channel 217 formed by inner surface 216 can be variously sized depending upon the application, which enables syringe handle 202 to be fitted to different brands and/or syringe sizes.

Top surface 212 and bottom surface 214 are configured such they can provide a seat for the flange 110 of a syringe 100. When syringe handle 200 is positioned for operation, either the top surface 212 or the bottom surface 214 abuts flange 110 of said syringe 100.

The grip portion 220 includes a first arm 230 and a second arm 240. The first arm 230 includes a connection point 232 opposite a distal end 234, an outer surface 236, and an axis B. The second arm 240 includes a connection point 242 opposite a distal end 244, an outer surface 246, and an axis C.

The first arm 230 is connected to the outer surface 218 of the hub portion 210 at connection point 232. The first arm 230 extends from outer surface 218 at connection point 232 and terminates at distal end 234. Distal end 234 is biased toward the top surface 212 of the hub portion 210. The second arm 240 is connected to outer surface 218, opposite the first arm 230, at connection point 242. In some embodiments, connection point 232 and connection point 242 are positioned on opposite sides of hub portion 210. The second arm 240 extends from outer surface 218 at connection point 242 and terminates at distal end 244. Distal end 244 is biased toward the bottom surface 214 of the hub portion 210.

Outer surface 236 and outer surface 246 may be of constant cross-section or contoured to facilitate the placement of fingers. Additionally, outer surface 236 and outer surface 246 may be textured by knurling or otherwise to improve grip, or may be covered in a material, such as rubber or soft plastic, that provides for increased grip by the user.

In various embodiments, the first arm 230, the second arm 240, or both may have various cross-sectional shapes along at least a portion of the arm including the entire length of the arm. For instance, in an exemplary embodiment, the first arm 230, the second arm 240 or both comprise an elliptical cross-section. In another exemplary embodiment, the first arm 230, the second arm 240, or both comprise a rectangular cross-section having rounded corners. In an exemplary embodiment, first arm 230 and second arm 240 are cylindrical bodies including circular cylindrical and elliptical cylindrical shapes. In at least one variant of such embodiments, axis B is the central longitudinal axis of the first arm 230 and axis C is the central longitudinal axis of the second arm 240 such that the axes of the first arm and second arm extend radially in planar alignment at 180 degrees from one another, along the central axis of the open-ended split-hub portion. In one variant of the exemplary embodiments, the first arm 230 and the second arm 240 may have cross sections that are non-circular, such that outer surface 246 in which case axis B is oriented along the length of the first arm 230 and passes through the center of gravity of the first arm 230 and axis C is oriented along the length of the second arm 240 and passes through the center of gravity of the second arm 240. In an exemplary embodiment, the first arm 230, the second arm 240 or both may have a continuous, smooth and uninterrupted exterior surface along at least a portion of each arm, including the entire length of the arm. In at least one exemplary embodiment at least a portion of the exterior surface of the first arm 230, the second arm 240, or both comprises a textured portion to advantageously enhance a user's ability to hold and operate the device without added strain.

The first arm 230 of the grip portion 220 extends radially from the outer surface 218 of the hub portion 210 such that the distal end 234 is biased with respect to axis A and toward the top surface 212 of the hub portion 210, forming angle 250 between axis A and axis B. In various embodiments, the angle 250 is greater than 0 degrees and less than 90 degrees. In some embodiments, the angle 250 formed between axis A and axis B is from 20 to 65 degrees. In some embodiments, the angle 250 is from 30 to 50 degrees. In some embodiments, the angle 250 is from 30 to 40 degrees. In some embodiments, the angle 250 is from 55 to 65 degrees. In an exemplary embodiment, the first arm 230, the second arm 240 or both extend radially from a connection point on the hub portion 210. Accordingly, the cross-sectional area of the first arm 230, the second arm 240, or both, at the connection point may be located entirely between the top surface and bottom surface of the hub portion.

The second arm 240 of the grip portion 220 extends radially from the outer surface 218 of the hub portion 210 such that the distal end 244 is biased along the direction of axis A and toward the top surface 212 of the hub portion 210, forming angle 252 between axis A and axis C. In various embodiments, the angle 252 is greater than 90 degrees and less than 180 degrees. In some embodiments, the angle 252 formed between axis A and axis C is from 110 to 150 degrees. In some embodiments, the angle 252 formed between axis A and axis C is from 120 to 40 degrees. In some embodiments, the angle 252 formed between axis A and axis C is from 135 to 145 degrees. In some embodiments, angle 250 is the supplement to angle 252 such that the sum of angle 250 and angle 252 is 180 degrees.

In some embodiments, the first arm 230 and the second arm 240 are configured to be parallel such that axis B and axis C are parallel to each other. In other embodiments, the first arm 230 and the second arm 240 may be configured in parallel such that axis B and axis C are coincident.

FIGS. 6-9 illustrate another embodiment of a syringe handle 300. Syringe handle 300 is similar to the assembly shown in FIGS. 2-5 and common elements have similar reference numerals as the embodiment shown in FIGS. 2-5.

The outer surface 336 of the first arm 330 and the outer surface 346 of the second arm 340 have a U-shaped cross section defining cavity 360 in the first arm 330 and cavity 362 in the second arm. Both cavity 360 and cavity 362 are filled with a number of ribs 364 to increase strength and rigidity of the first arm 330 and the second arm 340.

Figure 10:
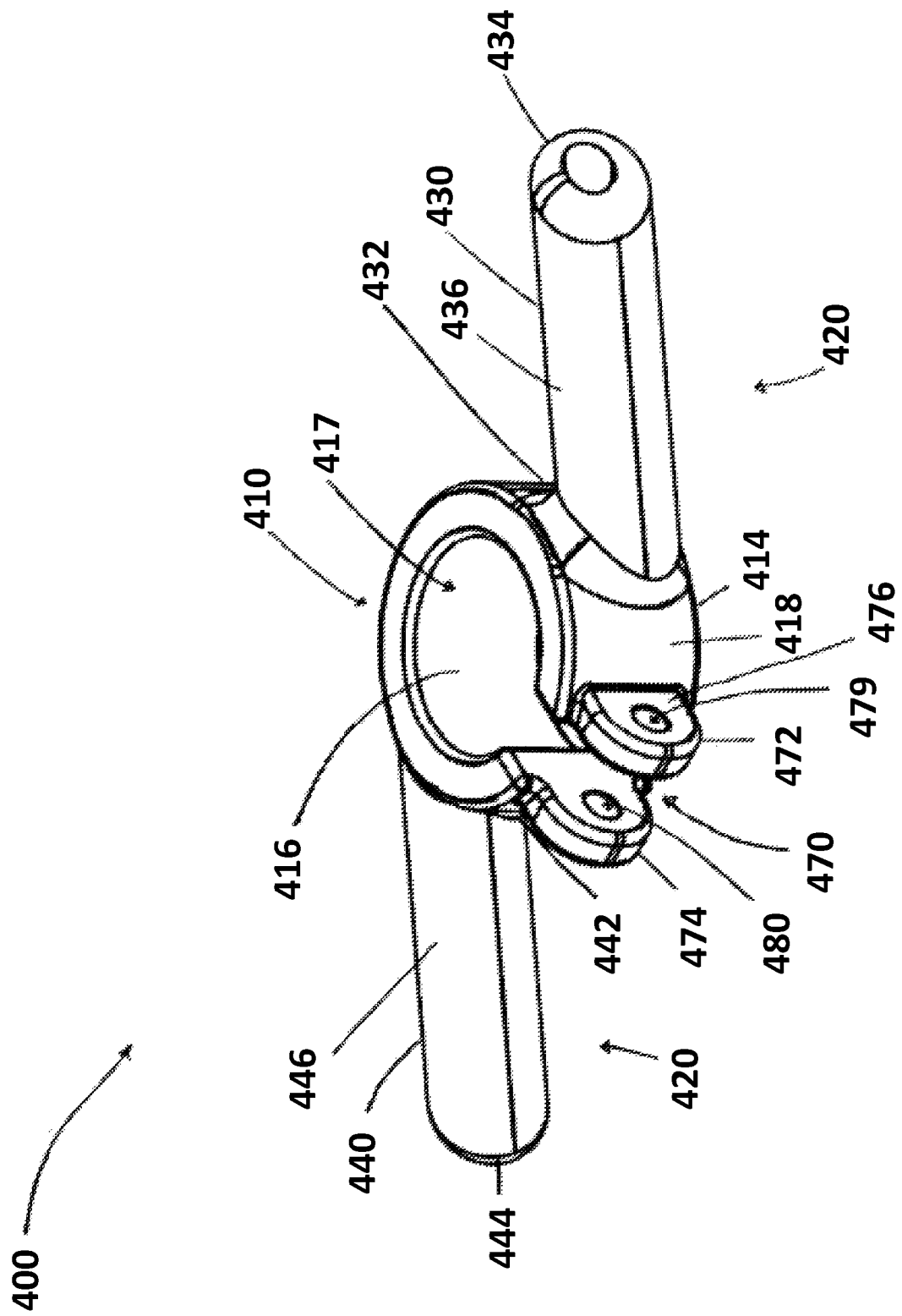
FIG. 10 is a front perspective view of another example embodiment of a syringe handle.

FIG. 10 illustrates another embodiment of syringe handle 400. Syringe handle 400 is similar to the assembly shown in FIGS. 2-5 and common elements have similar reference numerals as the embodiment shown in FIGS. 2-5.

The inner surface 416 of the hub portion further defines a slit 470 to allow for the expansion of the hub portion 410 to accommodate different brands and/or sizes of syringes. Slit 470 is positioned along outer surface 418 of the hub portion and extends through the channel 417 defined by inner surface 416. In some embodiments, the slit 419 is centered on the midway point between the first arm 430 and the second arm 440 on the outer surface of the hub portion 410. In other embodiments, it may be desirable to have the slit 470 located in such a position that slit 470 is biased toward either the first arm 430 or the second arm 440 of the grip portion 420.

The hub portion shown in FIG. 10 may further include a first flange 472 and second flange 474. The first flange 472 extends from and is connected to a side of slit 470 and the second flange 474 extends from and is connected to the opposite side of slit 470. In some embodiments the distance between the first flange 472 and the second flange 474 is fixable. In such embodiments the first flange 472 includes an outer face 476 defining hole 478, and the second flange 474 defines a threaded hole 480. Hole 478 is sized to allow a bolt to pass through such that the threads of said bolt engage threaded hole 480 while the head of said bolt engages outer face 476. In other embodiments the distance between flange 472 and flange 474 may be fixable by another method, including, but not limited to, a clasp, buckle, pin, or clamp.

In other embodiments, a syringe handle may be integrated with a syringe that includes a hub portion and a grip portion. In such embodiments, the hub portion is the body portion of the syringe and includes a barrel portion having an open end configured to receive a plunger, a necked portion configured to receive a needle and an outside surface. The barrel portion is generally cylindrical and further defines a central axis along its length. Where the barrel portion is not cylindrical, the barrel portion defines an axis along its length such that said axis passes through the center of gravity of the barrel portion. Each of the first arm and the second arm can be arranged and configured as described above with reference to FIGS. 2-9.

The grip portion includes a first arm and a second arm near the open end of the hub portion. Each of the first arm and the second arm include an end defining a connection point, a distal end, and an outer surface. The first arm is integrally connected to the outer surface of the barrel portion at a connection point near the open end. The second arm is integrally connected to the outer surface of the barrel portion on the outer surface of the barrel portion at a connection point opposite the first arm connection point. The first arm extends from the outer surface of the barrel portion in a radial manner and is biased towards the open end of the hub portion, terminating at a distal end. The second arm extends from the outer surface of the barrel portion in a radial manner and is biased towards the necked end of the body portion, terminating at a distal end.

It will be clear that the systems and methods described herein are well adapted to attain the ends and advantages mentioned as well as those inherent therein. Those skilled in the art will recognize that the systems within this specification may be implemented in many manners and as such is not to be limited by the foregoing exemplified embodiments and examples. In this regard, any number of the features of the different embodiments described herein may be combined into one single embodiment and alternate embodiments having fewer than or more than all of the features herein described are possible.

While various embodiments have been described for purposes of this disclosure, various changes and modifications may be made which are well within the scope contemplated by the present disclosure. Numerous other changes may be made which will readily suggest themselves to those skilled in the art and which are encompassed in the spirit of the disclosure.

What is claimed is:

1. A syringe handle comprising:
   a hub portion defining an outer surface, an inner surface, a top surface and a bottom surface, the inner surface being curved and configured to receive a portion of a syringe body; and
   each of the top surface and the bottom surface being adjacent to both the outer surface and the inner surface;
   a grip portion including a first arm and a second arm,
   each of the first arm and the second arm being connected to and extending from the outer surface of the hub portion;
   the first arm having a first arm distal end biased toward the top surface of the hub portion; and
   the second arm having a second arm distal end biased toward the bottom surface of the hub portion,
   wherein in a first operational position the top surface of the hub portion abuts a flange of a syringe and in a second operational position the bottom surface of the hub portion abuts the flange of the syringe, and
   wherein the entire syringe handle is monolithic.

2. The syringe handle according to claim 1, the hub portion defining an expansion slit configured to enable expansion of the hub portion when positioned on the syringe body.

3. The syringe handle according to claim 2, the hub portion having a first flange and a second flange extending from the outer surface of the hub portion on each side of the expansion slit such that the first flange and the second flange are moveable towards each other.

4. The syringe handle according to claim 3, wherein a relative position of the first flange and the second flange is fixable.

5. The syringe handle according to claim 1, the first arm and the second arm of the grip portion being positioned on opposite sides of the hub portion.

6. The syringe handle according to claim 1, the first arm and the second arm of the grip portion each having an ergonomic outer surface portion that is contoured or textured.

7. The syringe handle according to claim 1, wherein a first arm angle formed between the central axis of the first arm and the central axis of the hub portion is greater than 0 degrees and less than 90 degrees, and a second arm angle formed between the central axis of the second arm and the central axis of the hub portion is greater than 90 degrees and less than 180 degrees.

8. The syringe handle according to claim 7, such that the first arm angle is greater than 55 degrees and less than 65 degrees, and the second arm angle is greater than 135 degrees and less than 145 degrees.

9. The syringe handle according to claim 7 wherein the central axis of the first arm and the central axis of the second arm of the grip portion are parallel.

10. The syringe handle according to claim 7, wherein the central axis of the first arm and the central axis of the grip portion are coincident.

11. The syringe handle according to claim 1, wherein the first arm and the second arm of the grip portion comprise a rectangular cross-section with rounded corners.

12. The syringe handle according to claim 1, comprising a split cylindrical center hub.

13. The syringe handle of claim 1, wherein each of the first and second arms have a central axis extending along the entire length of the arm, and wherein each of the central axis of the first arm and second arm extends through the hub portion.

14. The syringe handle of claim 1, wherein the syringe handle is configured to freely rotate circumferentially about the syringe in the first operational position and in the second operational position.

15. A syringe handle comprising:
a hub portion defining an outer surface, an inner surface, a top surface and a bottom surface, the inner surface being curved and configured to receive a portion of a syringe body; and each of the top surface and the bottom surface being adjacent to both the outer surface and the inner surface;
a grip portion including a first arm and a second arm;
each of the first arm and the second arm being connected to and extending from the outer surface of the hub portion;
the first arm having a first arm distal end biased toward the top surface of the hub portion; and
the second arm having a second arm distal end biased toward the bottom surface of the hub portion;
wherein the first arm and the second arm of the grip portion comprise an elliptic cylinder.

16. A syringe handle comprising:
a hub portion defining an outer surface, an inner surface, a top surface and a bottom surface, the inner surface being curved and configured to receive a portion of a syringe body; and
each of the top surface and the bottom surface being adjacent to both the outer surface and the inner surface;
a grip portion including a first arm and a second arm,
each of the first arm and the second arm being connected to and extending from the outer surface of the hub portion;
the first arm having a first arm distal end biased toward the top surface of the hub portion; and
the second arm having a second arm distal end biased toward the bottom surface of the hub portion, and
wherein in a first operational position the top surface of the hub portion abuts a flange of a syringe and in a second operational position the bottom surface of the hub portion abuts the flange of the syringe,
wherein the syringe handle is configured to freely rotate circumferentially about the syringe in the first operational position and in the second operational position, and
wherein in the first operational position and in the second operational position, the syringe handle is configured to permit the user to depress a plunger of the syringe by placing the thumb on the plunger and a number of fingers on the first arm and second arm to deliver the contents of the syringe.

* * * * *